United States Patent
Chekanov

(10) Patent No.: US 6,540,666 B1
(45) Date of Patent: Apr. 1, 2003

(54) ADAPTIVE DEVICE FOR SUPPORTING CARDIAC FUNCTION DURING DIASTOLIC DYSFUNCTION AND METHOD THEREFOR

(75) Inventor: Valeri S. Chekanov, Franklin, WI (US)

(73) Assignee: Heart Care Associates, LLC, Milwaukee, WI (US)

( * ) Notice: Subject to any disclaimer, the term of this patent is extended or adjusted under 35 U.S.C. 154(b) by 0 days.

(21) Appl. No.: 10/041,225

(22) Filed: Jan. 8, 2002

(51) Int. Cl.$^7$ .................................................. A61F 2/00
(52) U.S. Cl. ........................................................ 600/37
(58) Field of Search ...................... 600/374, 37, 16–18; 607/2, 129; 601/153; 602/2, 9, 116, 149, 129, 16–17; 623/66, 1, 2, 11; 128/897–899; 606/151

(56) References Cited

U.S. PATENT DOCUMENTS

| | | | |
|---|---|---|---|
| 5,738,626 A | 4/1998 | Jarvik | |
| 5,800,528 A | 9/1998 | Lederman et al. | |
| 6,076,013 A | * 6/2000 | Brennan et al. | 607/2 |
| 6,095,968 A | 8/2000 | Snyders | |
| 6,132,363 A | 10/2000 | Freed et al. | |
| 6,165,122 A | 12/2000 | Alferness | |
| 6,193,648 B1 | 2/2001 | Krueger | |
| 6,206,820 B1 | 3/2001 | Kazi et al. | |
| 6,241,654 B1 | * 6/2001 | Alferness | 600/37 |

* cited by examiner

Primary Examiner—Max F. Hindenburg
Assistant Examiner—Nikita R Veniaminov
(74) Attorney, Agent, or Firm—Sonali Srivastava; Godfrey & Kahn, S.C.

(57) ABSTRACT

An adaptive heart binding device and method for the treatment of heart failure. The device has a non-distendible jacket to prevent the heart from expanding beyond a preselect volume. A first chamber corresponding the right ventricle and a second chamber corresponding to the left ventricle are located between the heart and the jacket. The first and second chamber can be inflated to exert additional pressure on the heart over time without additional surgery. The gradual pressure increase hemodynamically remodels the heart so that is performs more like a non-diseased heart. The binding device can be used as a bridge to or in place of heart transplant.

18 Claims, 14 Drawing Sheets

ADAPTIVE DEVICE FOR SUPPORTING CARDIAC FUNCTION DURING DIASTOLIC DYSFUNCTION AND METHOD THEREFOR

FIELD OF THE INVENTION

The present invention pertains to a method and apparatus for treating congestive heart disease and related valvular dysfunction. More particularly, the present invention is directed to an adaptive cardiac constraint having an outer non-extentible device and a pair of inner inflatable members for preventing over-extension of the heart during diastole.

BACKGROUND OF THE INVENTION

Congestive heart disease is a progressive and debilitating illness. The disease is characterized by a progressive enlargement of the heart. As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves may not adequately close. This impairs the function of the valves and further reduces the heart's ability to supply blood.

Causes of congestive heart failure (CHF) are not fully known. In certain instances, CHF may result from viral infections. In such cases, the heart may enlarge to such an extent that the adverse consequences of heart enlargement continue after the viral infection has passed and the disease continues its progressively debilitating course.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The heart H' has four internal heart chambers including a right atrium RA', a left atrium LA', a right ventricle RV' and a left ventricle LV'. The heart H' has a length measured along a longitudinal axis BB'-AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V (atrio-ventricular) groove AVG'. Extending away from the upper portion UP' are plurality of major blood vessels communicating with the chambers RA', RV', LA', LV'. For ease of illustration, only the superior vena cava SVC', inferior vena cava IVC' and one of the left pulmonary vein LPV' are shown as being representative.

The heart H' contains valves to regulate blood flow between the chambers RA', RV', LA', LV' and between the chambers and the major vessels, aorta and preliminary artery. For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radically outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Comparing, FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H dilates outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively less efficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive dilation of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

Patients suffering from CHF are commonly grouped into four classes (i.e., Classes I, II, III and IV). In the early stages (e.g., Classes I and II), drug therapy is the most commonly prescribed treatment. Drug therapy treats the symptoms of the disease and may slow the progression of the disease. However, drugs may have adverse side effects. There is no cure for CHF; even with drug therapy, the disease will progress.

CHF is encountered with increasing frequency. Most of this increase can be attributed to the aging population. An estimated 4–5 million people in the United States have CHF with 400,000 new cases annually. This is an estimated 2,000 new cases annually per 1.5 million people. For those with advanced CHF, mortality is at an extremely high level with a 1-year mortality rate of 66%, and a 2-year mortality rate of 82%. The survival rate in patients with new onset heart failure after acute myocardial infarction is even lower, with only a small minority remaining alive after five years.

Thirty years ago, surgeons began actively developing techniques to treat pre-end stage CHF. Between 1967 and 1980, three unique clinical techniques were developed: heart transplantation, a mechanical assist system, and the artificial heart. The only permanent treatment for congestive heart disease is heart transplant.

Between 1985 and 1998, three other clinical options were developed: cardiomyoplasty, partial left ventriculectomy, and mechanical support devices such as plastic ventricular binding. Cardiomyoplasty is a treatment for earlier stage congestive heart disease (e.g., as early as Class III dilated cardiomyopathy). In this procedure, the latissimus dorsi muscle (taken from the patient's back) is wrapped around the heart and chronically paced synchronously with ventricular systole. Pacing of the muscle results in muscle contraction to assist the contraction of the heart during systole.

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive, requires costly cardiomyostimulators, and is complicated. For example, it is difficult to adequately wrap the muscle around the heart with a satisfactory fit. Also, if adequate blood flow is not maintained to the wrapped muscle, the muscle may necrose. The muscle may stretch after wrapping, reducing its constraining benefits. Further, the muscle is generally not susceptible to post-operative adjustment. Finally, the muscle may fibrose and adhere to the heart causing undesirable constraint on the contraction of the heart during systole.

Partial left ventriculectomy is a surgical technique that includes dissecting and removing portions of the left ventricles in order to reduce heart volume. This radical new and experimental procedure subject to substantial controversy. Furthermore, the procedure is highly invasive, risky and expensive, and commonly includes other expensive procedures such as a concurrent heart valve replacement. This treatment is limited to Class IV patients, and accordingly, provides no hope to patients facing ineffective drug treatment prior to Class IV. If the procedure fails, emergency heart transplant is the only available option.

Despite the recent innovations, cardiac transplantation remains the technique of choice for the treatment of CHF. To qualify, a patient must be in the later stage of the disease (e.g., Classes III and IV, with Class IV patients given priority for transplant). Such patients are extremely sick individuals. Class III patients have marked physical activity limitation, and Class IV patients are symptomatic even at rest. Unfortunately, there is an inadequate supply of transplantable hearts for CHF patients. This increases the need for treatments that can bridge heart function between the time a heart is needed to the time a transplantable heart is available.

Mechanical support devices such as prosthetic heart binding are primarily used in intermediate procedures for treating congestive heart disease. Prosthetic cardiac binding is a procedure for applying a girdle to support a dilated heart. While still experimental, cardiac binding has promise for CHF patients.

For example, U.S. Pat. No. 5,702,343, dated Dec. 30, 1997, and U.S. Pat. No. 5,800,528, dated Sep. 1, 1998, teach a passive jacket to constrain cardiac expansion during diastole. These cardiac constraint devices can be placed on an enlarged heart and snugly fitted during diastole. However, such bindings are non-flexible and compress the diastolic heart at a constant pressure. If the diastolic heart is too tightly compressed during a single step procedure, it will likely arrest. Alternatively, if the diastolic heart is too weakly compressed during the single step procedure, initial positive results will revert to baseline heart failure after only several days. Performing multiple heart surgeries to gradually increase the pressure is not feasible.

A more flexible device is that seen in U.S. Pat. No. 6,193,648, dated Feb. 27, 2001. This device is a knit "jacket" that can be loosely slipped onto the heart. The heart may be pre-shrunk prior to placement of the device, or the device may be fitted on the heart without pre-shrinking the heart. The device is adjusted to a snug fit on the heart during diastole. Even though the device is more flexible, the disadvantage of this device is that it cannot be readjusted at a later date.

U.S. Pat. No. 6,206,820 dated Mar. 27, 2001, to Kazi, discloses a device for supporting cardiac function that is adaptable to the hemodynamic changes of the heart after surgery. However, this device is limited to only a selective part of the left ventricle of the heart, and only assists the heart during ventricle systole (contraction). The Kazi device does nothing for a failed heart during ventricular diastole because it cannot provide compression during diastole.

Accordingly, a need exists for a heart-binding device that can incrementally add compression to a failed heart during diastole to adjust to the hemodynamic changes of the heart over time.

SUMMARY OF THE INVENTION

A surgical method and device are disclosed for treating congestive heart disease. In general, an adaptive constraining device is placed on the heart. The device is a binding that covers the left and right ventricles, and which has an expandible chamber adjacent to each ventricle. The device allows the gradual increase of compression on the dilated heart while administering separate loads on the left and right ventricles. The gradual increase allows the heart to be hemodynamically remodeled so that the blood flow through the heart becomes more normal without the problems associated with the application of one-step compression.

By improving the hemodynamic function of the diseased heart by one-third to one-half, a reduction in the rate of one-year mortality for the patient is expected. In addition, days of hospitalization per year, and costs to government health systems for these patients, may be decreased by 75% or more due to reduced dependence on expensive drug therapy, improved mental function, and improved lifestyle.

While the present invention is particularly useful for case of heart failure, other applications are possible and references to use with diastolic heart failure of the ventricles should not be deemed to limit the application of the present invention. The present invention may be advantageously adapted for use where similar performance capabilities and characteristics are desired. These and other objects and advantages of the present invention will become apparent from the detailed description, claims, and accompanying drawings.

DESCRIPTION OF THE PREFERRED EMBODIMENTS

A. Congestive Heart Therapy

Figure 1A:
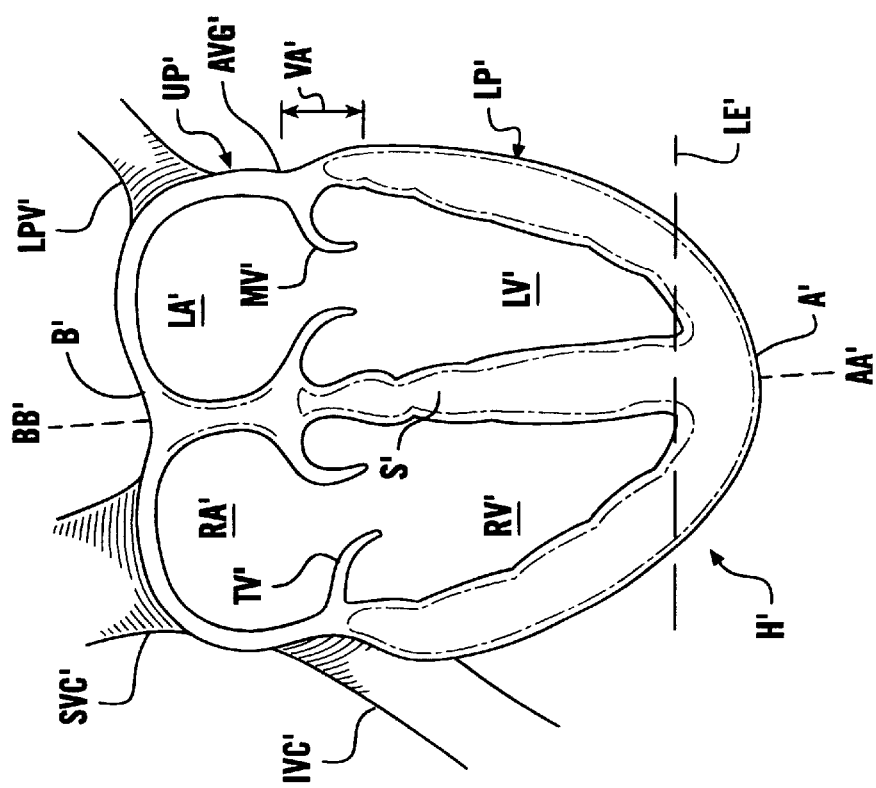
FIG. 1A is a cross-sectional front view of the human heart of FIG. 1 during diastole.
Figure 1:
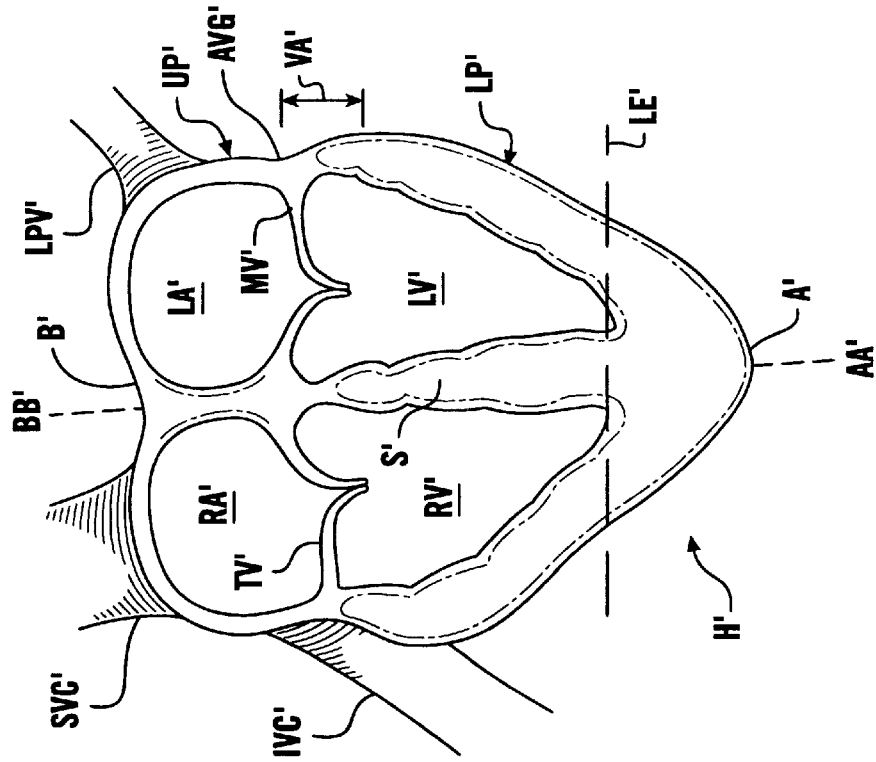
FIG. 1 is a cross-sectional front view of a normal human heart during systole.
Figure 2A:
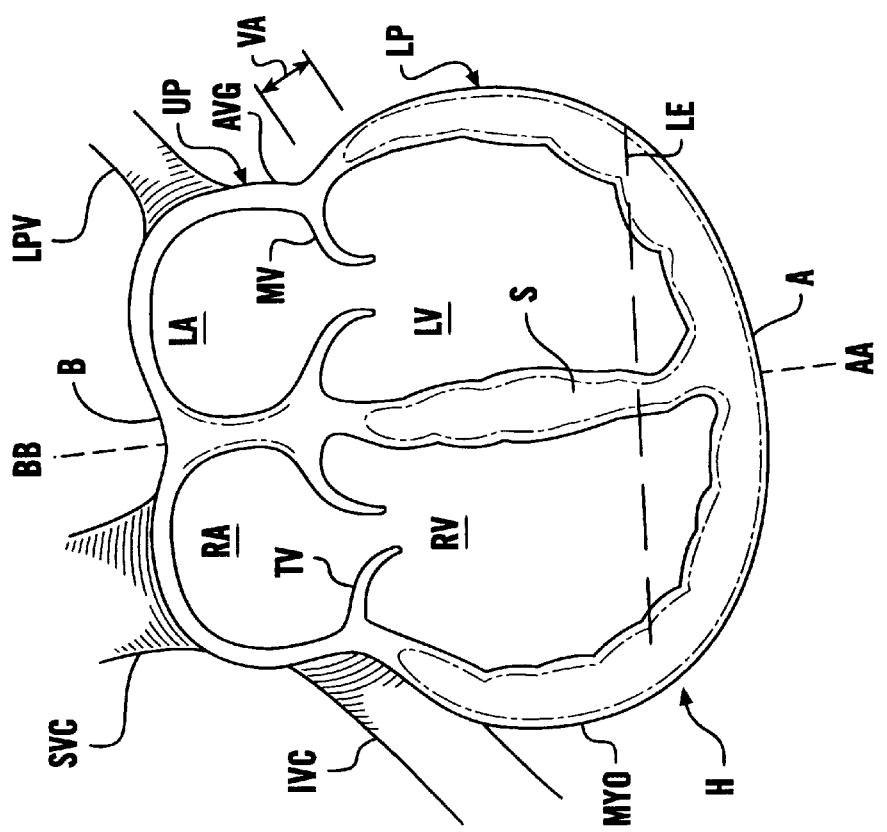
FIG. 2A is a cross-sectional front view of the human heart of FIG. 2 during diastole.
Figure 2:
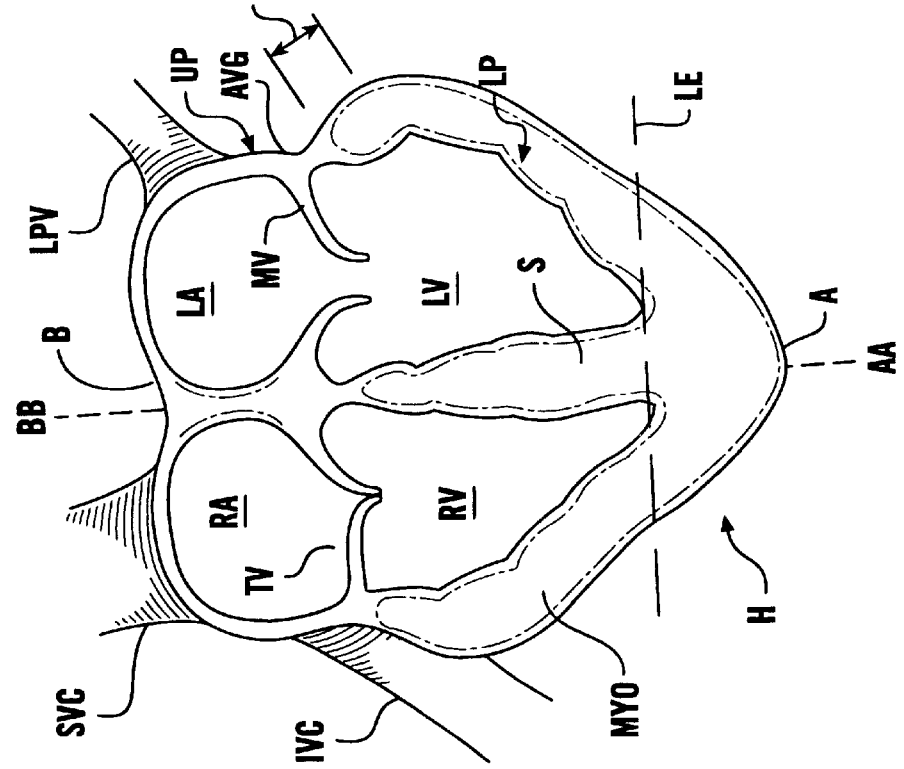
FIG. 2 is a cross-sectional front view of a human heart during systole and deformed by congestive heart disease.
Figure 3:
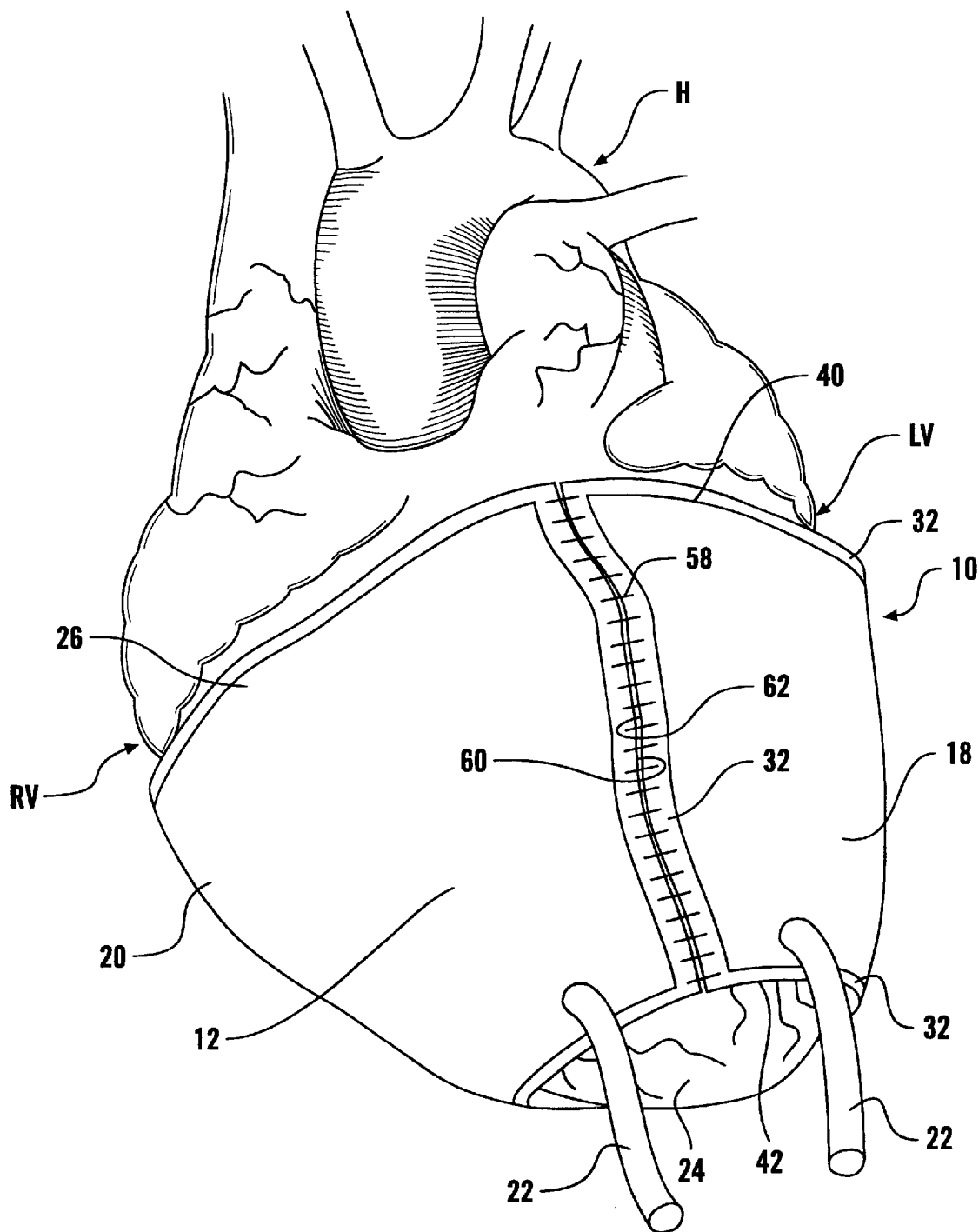
FIG. 3 is a front perspective view of the adaptive device of the present invention fit onto a human heart.

A treatment method and device for the treatment of CHF are described. The cardiac constraint device 10 shown in FIG. 3 is an adaptive binding of biologically compatible material, such as plastics used for surgical grade tubing, intravenous bags or the like. The device 10 partially covers the left and right ventricles, and gradually increases compression on the dilated heart by applying separate loads on the left and right ventricles. The device 10 is generally sized for the heart H' to be constrained within a particular volume 16. The device 10 can be wrapped around the heart H' and sutured together as described herein.

Figure 4:
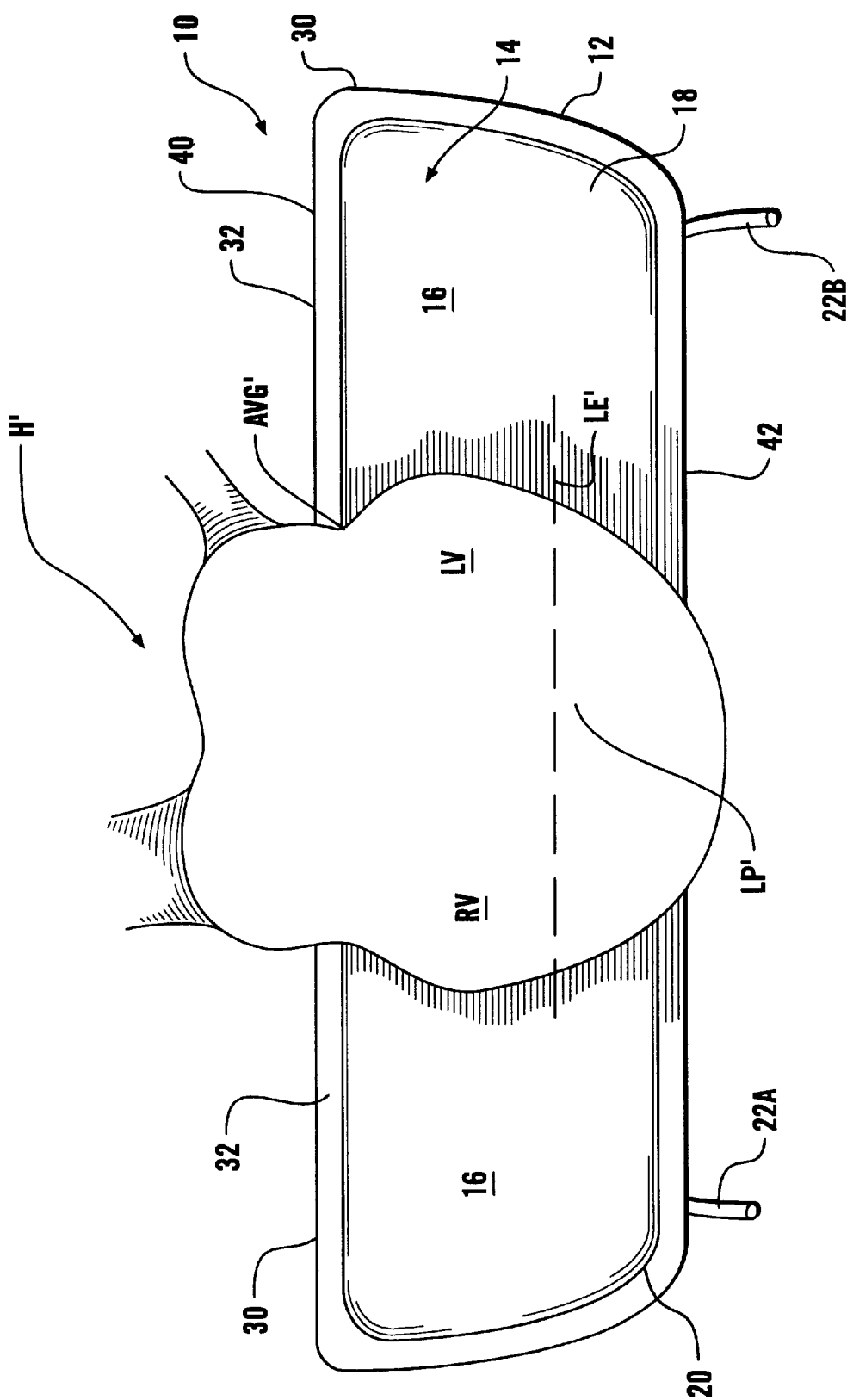
FIG. 4 is a front elevational view with the device shown in FIG. 3 opened to reveal the treated heart.
Figure 5:
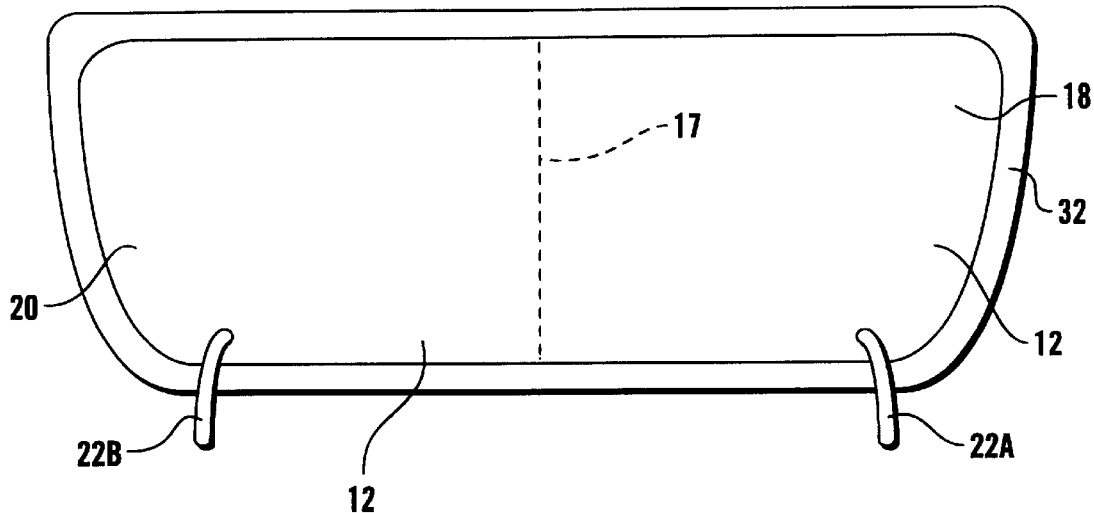
FIG. 5 is a rear elevational view of the open device shown in FIG. 3.
Figure 6:
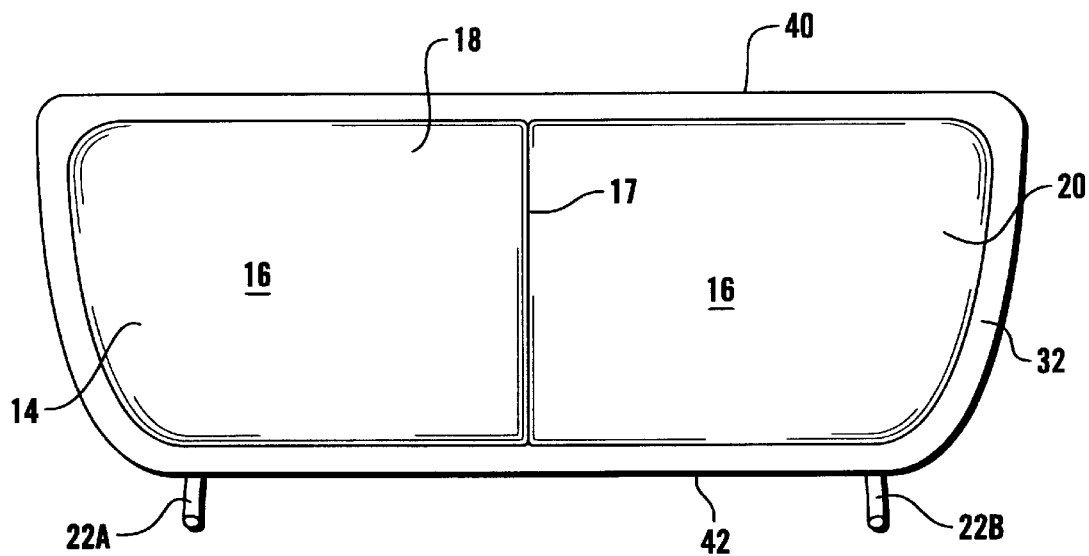
FIG. 6 is a front elevational view of the open device shown in FIG. 3.

With reference now to FIGS. 5 and 6, the cardiac constraint device 10 is shown as a jacket 12 of flexible yet non-distendible, biologically-compatible material, such as the type of plastic used in surgical implants or intravenus bags. The shape of device 10 can be varied widely, and should not be limited to the shape shown in FIGS. 4, 5 and 6. The interior side 14 of device 10 is an inner distendible membrane or wall 16. Wall 16 is divided by a seam 17 to create two separate chambers, namely a left chamber 18 and a right chamber 20. Each of a pair of supply tubes 22a, 22b is attached to respective chambers 18, 20. These supply tubes 22a, 22b allow liquid to be selectively introduced to or removed from one or both chambers 18, 20. A margin 32 is provided around the outer edges 30 of each chamber, to permit adjustability of size of the device upon installation. In the most preferred embodiment, the margin 32 is about 3 cm. wide. This margin 32 is preferably neither inflatable nor stretchable to any significant degree. Margin 32 is trimmable and allows the device to be custom fit with respect to a heart H to be treated.

Referring now to FIG. 4, each chamber 18, 20 is positioned to wrap around and over each ventricle so that in use, the left chamber 18 is adjacent to left ventricle LV and the right chamber 20 is adjacent the right ventricle RV. The device 10 has a length L between the upper end 40 and lower end 42. The upper end 40 of the device 10 preferably extends to the A-V groove, AVG. The lower end 42 preferably extends to a position in the lower portion LP to at least partially constrain the lower ventricular extremities located beyond dashed line LE'.

Figure 7:
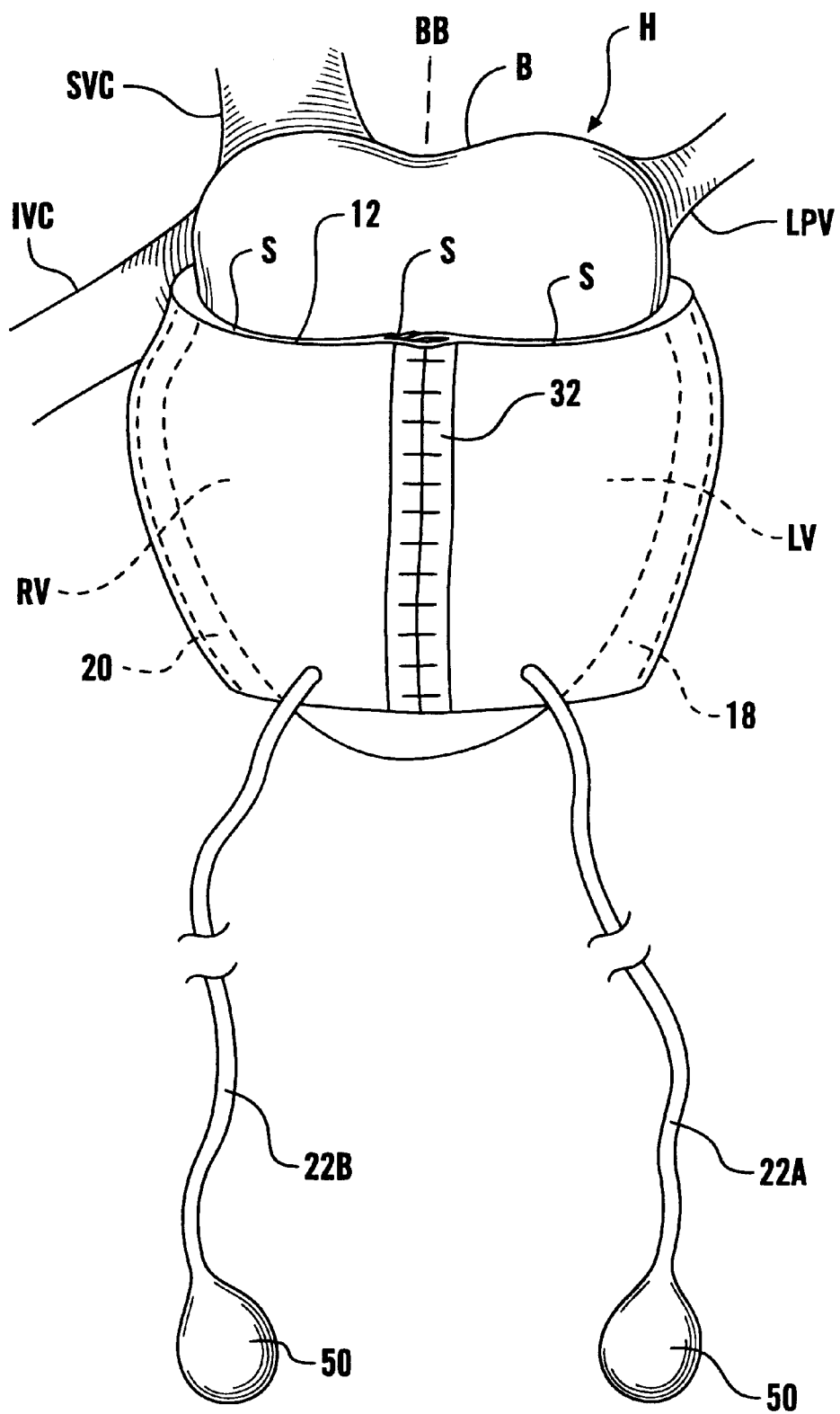
FIG. 7 is a front elevational view of an evenly-inflated device wrapped around a heart.

Referring now to FIG. 7, each chamber 18, 20 is in fluid communication with a respective non-distendible bladder 50a and 50b by means of respective supply tubes 22a and 22b. Each bladder 50, supply tube 22a, 22b and chamber 18, 20 are completely filled with a liquid, preferably sterile saline, so that no air bubbles are present. The bladders 50, 50b are located inside the patient's body, just underneath the skin. Thus, the pressure that device 10 can exert on a heart can be adjusted by injecting additional liquid or removing a desired amount of liquid from one or both of the bladders 50a, 50b. The biologically compatible material from which bladders 50a, 50b are constructed is self-sealing so that a puncture from a hypodermic needle stick will not cause the bladder contents to leak into the patient's body.

In operation, the differing stiffness and distention of the inner wall 16 of each chamber and the jacket 12 enables "heart remodeling." Once device 10 is wrapped around the heart to match the heart's initial volume and sutured together, the jacket 12 does not distend, but rather acts as an unyielding barrier to prevent any heart dilation. The distendible inner wall 16 conforms to the heart's surface. One or both chambers are filled with increasing amounts of liquid to exert increasing pressure on the heart. The outer, non-distendible wall of jacket 12 resists the additional pressure, while the inner, distendible walls of chambers 18, 20 distend with each selective increase or decrease in pressure on the walls of right and left ventricles.

B. Installation

The binding device 10 is installed surgically, preferably with a medial sternotomy without bypass. Opened jacket 12 is placed behind the heart with the left chamber 18 close to the left ventricle LV and the right chamber 20 close to the right ventricle RV. Jacket 12 is then wrapped about the heart and the two adjacent margins 32 sutured together using sutures 58 to compress the heart just above the anterior border between the left and right ventricles. Any excess material from margin 32 can be trimmed off after suturing is complete, leaving edges 60, 62 (FIG. 3).

Figure 9:
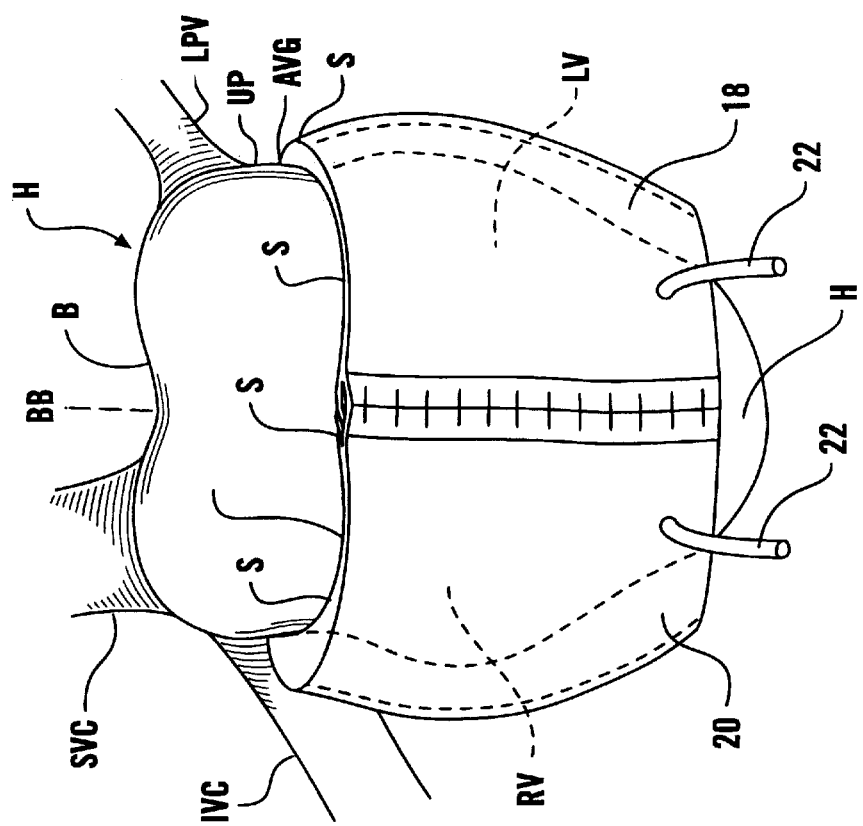
FIG. 9 is a front elevational view of the device shown in FIG. 7, wherein one chamber of the device is inflated more than the other chamber.
Figure 8A:
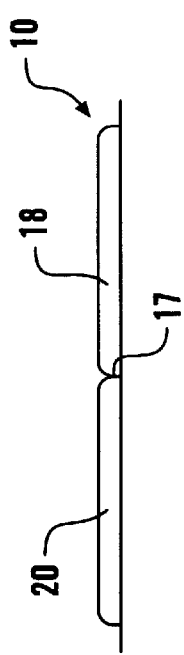
FIG. 8A is a schematic side elevation of the open device shown in FIG. 4, and equal pressure exerted by each chamber.
Figure 8B:
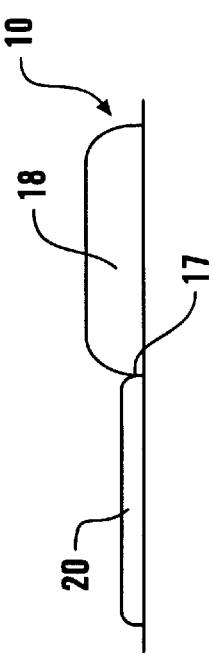
FIG. 8B is a schematic side elevation of the open device shown in FIG. 8A with a greater pressure on one chamber.
Figure 8C:
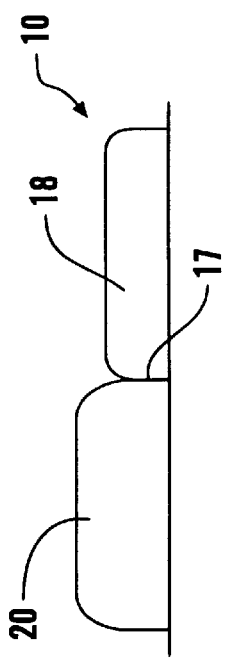
FIG. 8C is a schematic side elevation of the open device shown in FIG. 8A with a greater pressure on one chamber.

Referring now to FIG. 9, after the jacket 10 is positioned on the heart H, the upper edge 40 of the device 10 is preferably secured to the pericardium (not shown) using sutures (or other fastening means such as staples). Specifically, device 10 is preferably sutured to the pericardium at suture locations S circumferentially spaced along the upper end 40. While a surgeon may elect to add additional suture locations to prevent shifting of the device 10 after placement, the number of such locations S is preferably limited so that the device 10 does not restrict contraction of the heart H during systole.

Once in place, the decrease of left and right ventricular end-diastolic volume is monitored by echocardiography, or the like. Next, liquid is introduced into one or both of the bladders 50a, 50b and consequently into chambers 18 and/or 20 to change chamber pressure according to the hemodynamic data and cardiac function.

Using pulmonary vein pressure, central venous pressure, and right and left ventricular end-diastolic volume and pressure as indicators of the amount of heart compression, both chambers 18, 20 of the device 10 are filled with the appropriate amount of liquid. After several days, as the heart adapts to the compression applied by device 10, it tends to shrink, which has the effect of reducing the pressure exerted by the device 10 on the heart H. Thus, filling of one or both of the chambers 18, 20 is repeated to further decrease heart dilatation. Each subsequent filling will re-exert pressure on the right and left ventricles, which will allow for the heart's adaptive cardiac remodeling to a heart sized in the normal range. Adaptive cardiac remodeling is achieved by filling the chambers repeatedly to decrease the heart's dilatation gradually.

Figure 10:
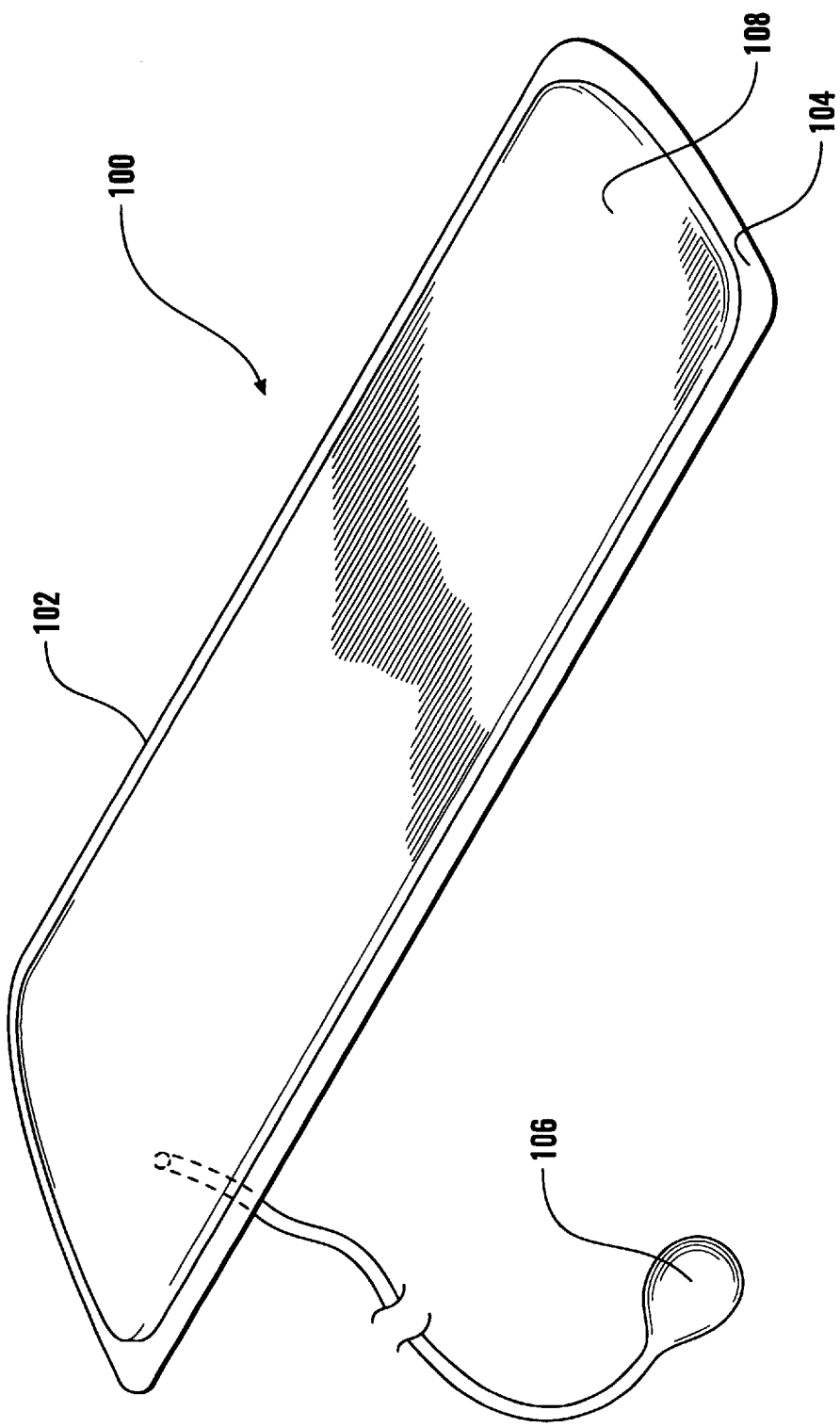
FIG. 10 is an alternative embodiment of the invention having a single ventricular chamber.
Figure 11:
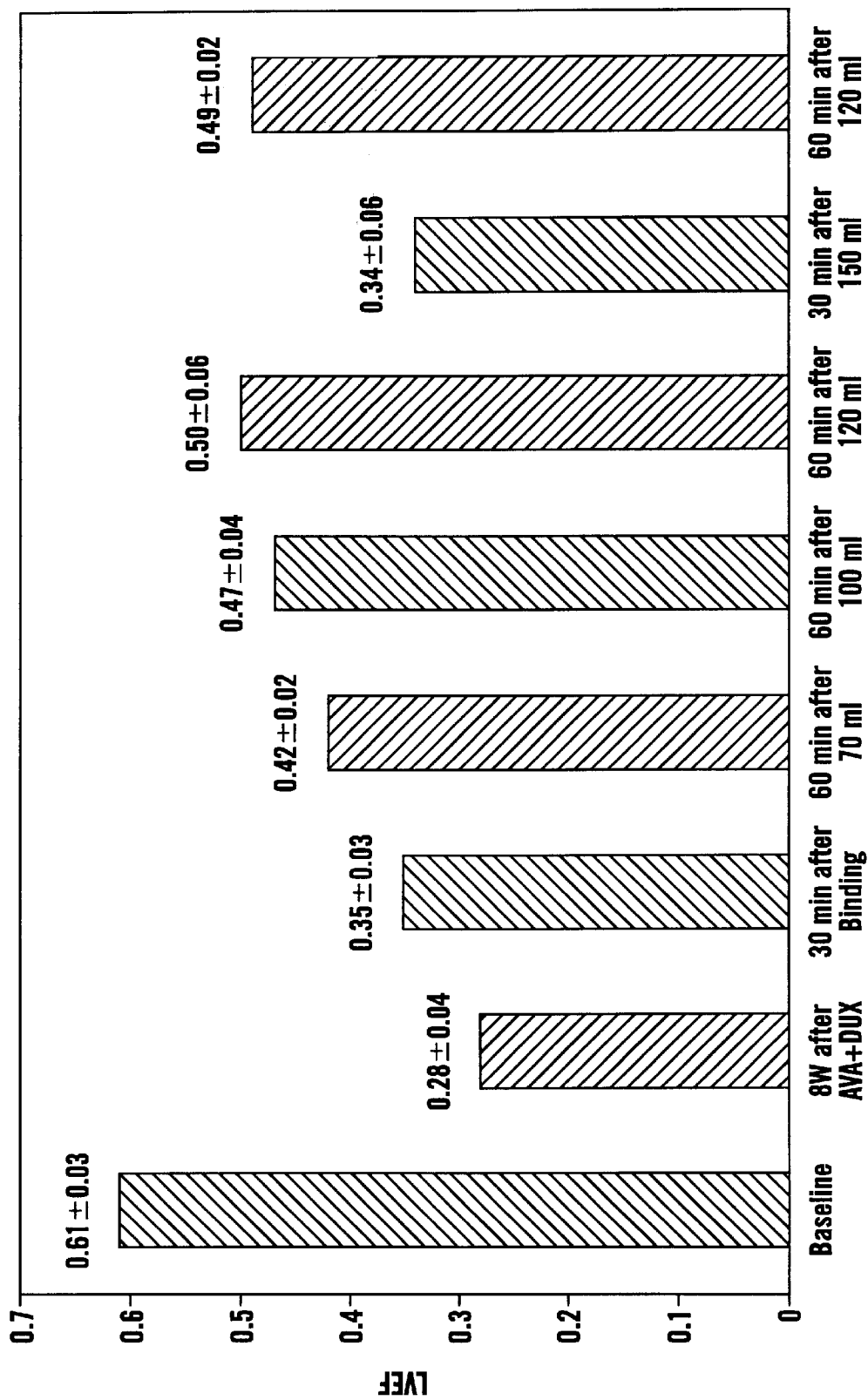
FIG. 11 is a chart showing left ventricular ejection fraction versus various levels of ventricular compression.
Figure 12:
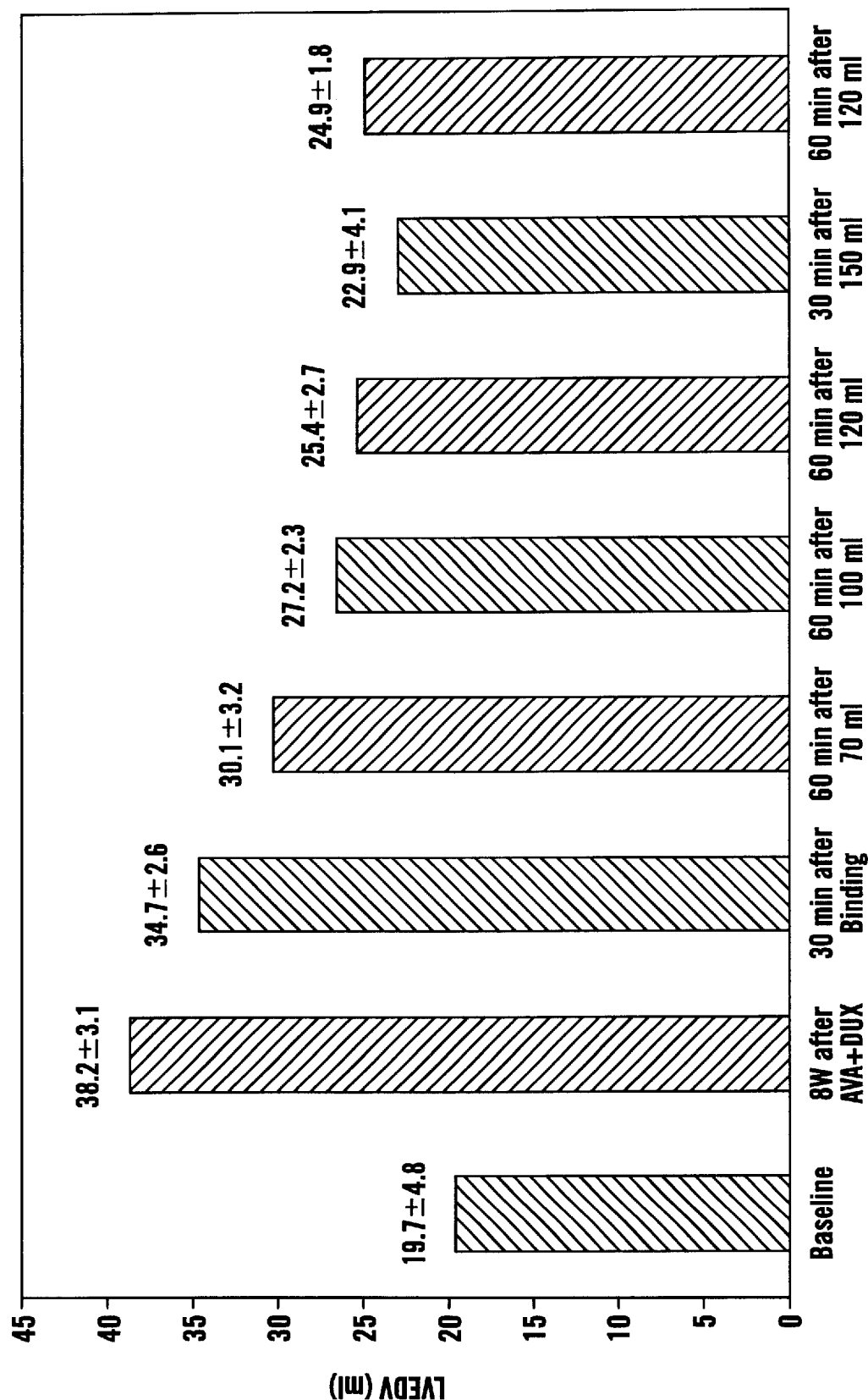
FIG. 12 is a chart showing left ventricular end diastolic volume versus various levels of ventricular compression.
Figure 13:
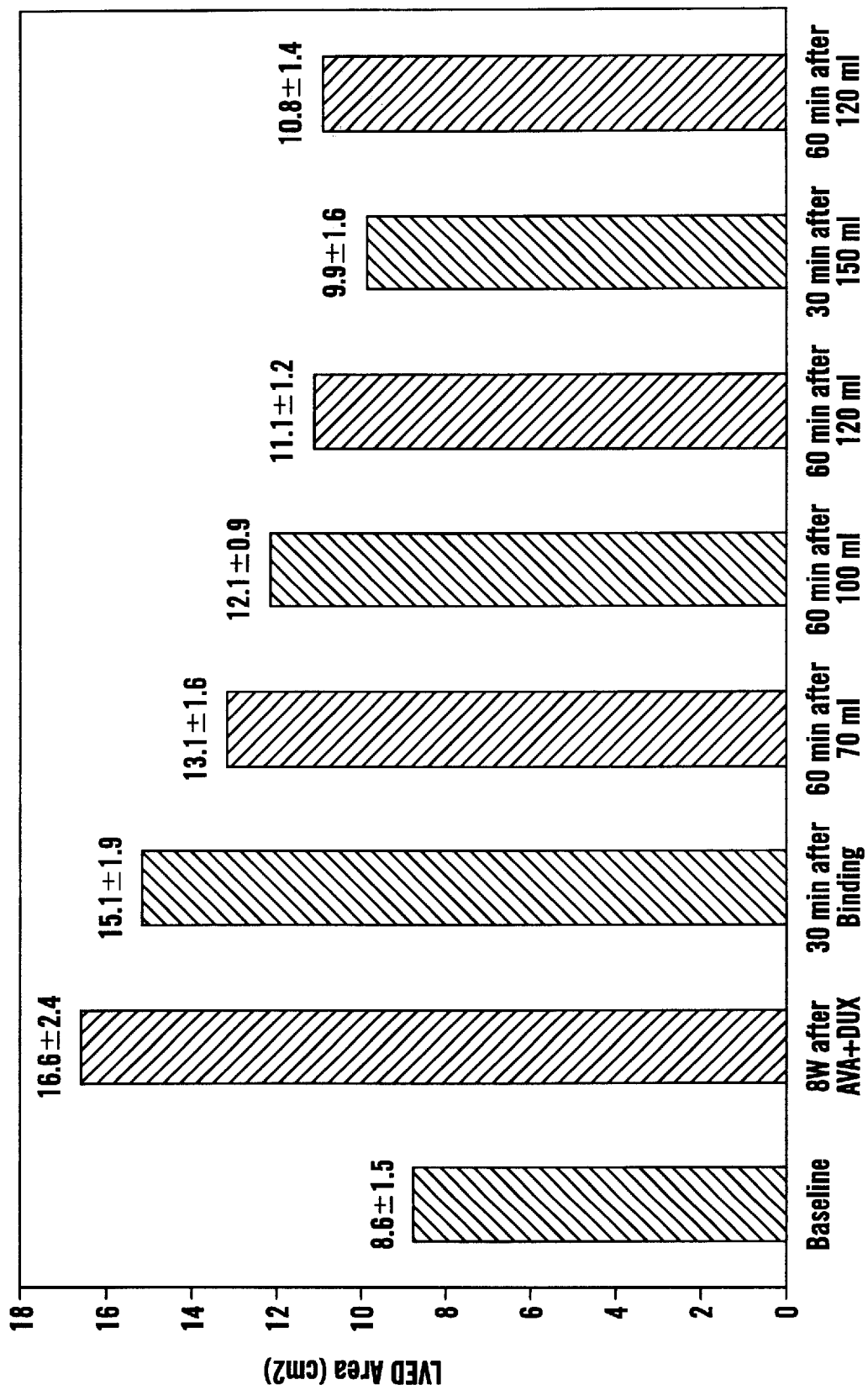
FIG. 13 is a chart showing left ventricular end diastolic area versus various levels of ventricular compression.
Figure 14:
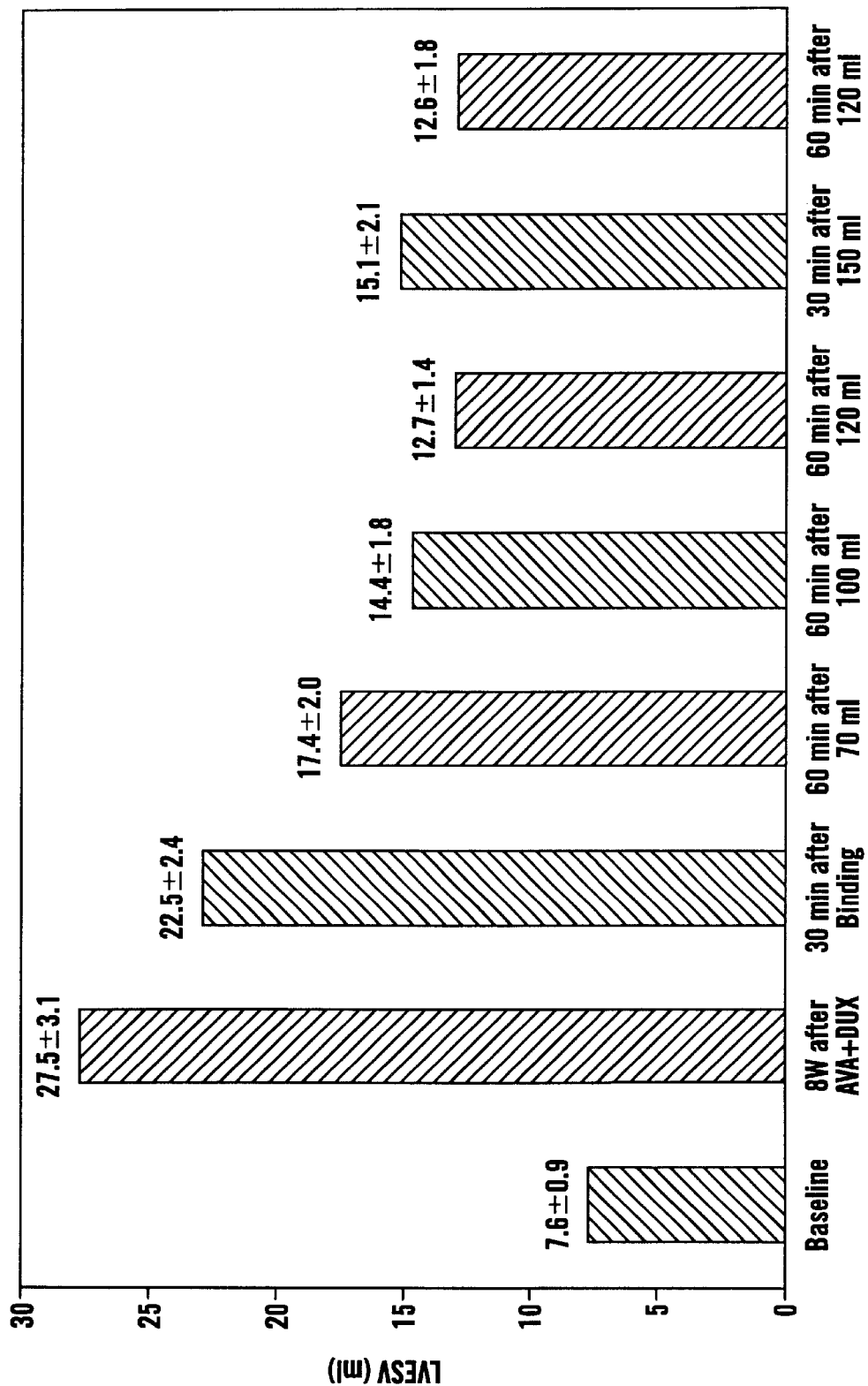
FIG. 14 is a chart showing left ventricular end systolic volume versus various levels of ventricular compression.
Figure 15:
FIG. 15 is a chart showing left ventricular end systolic area versus various levels of ventricular compression.
Figure 16:
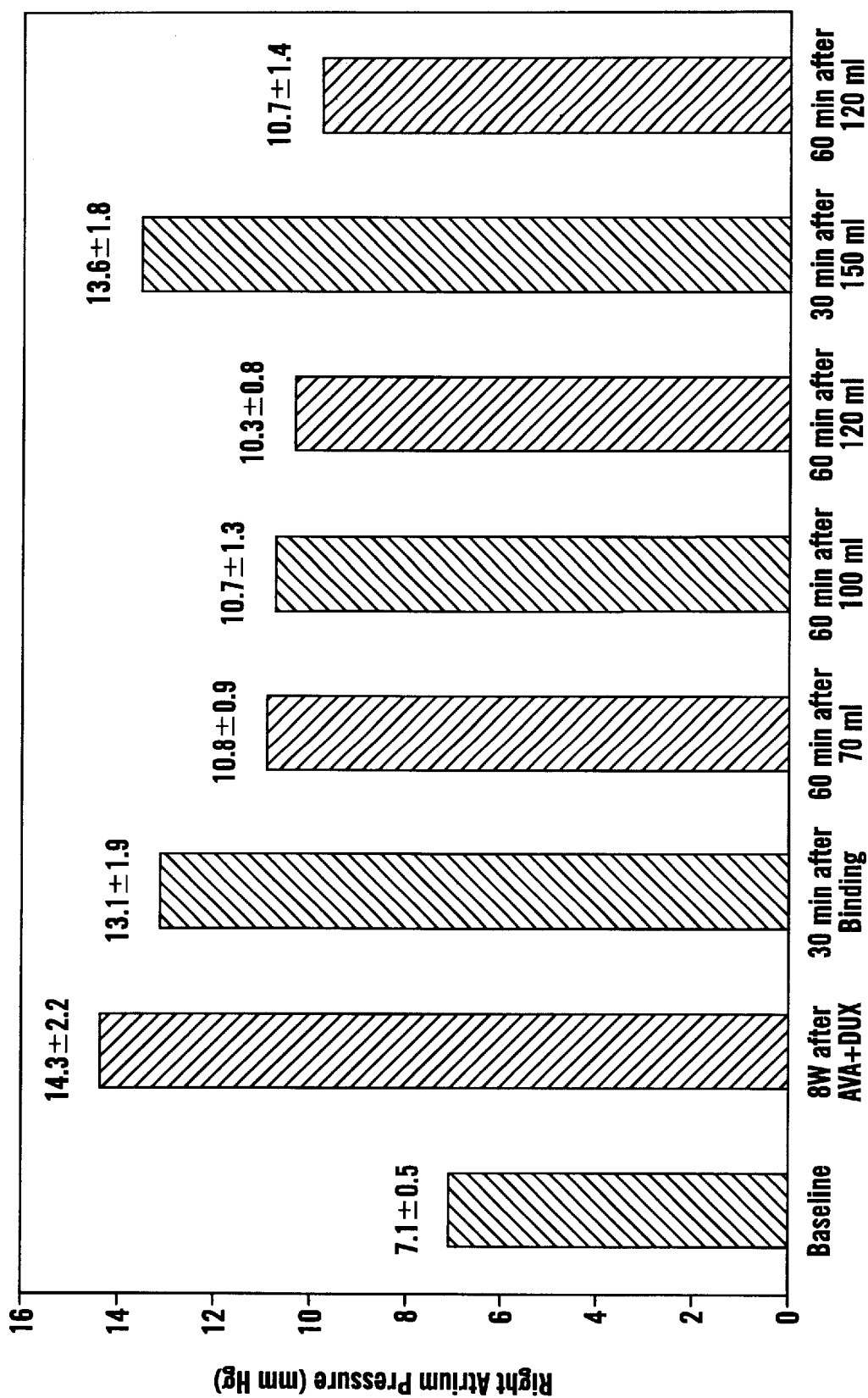
FIG. 16 is a chart showing right atrium pressure versus various levels of ventricular compression.

In another embodiment of the present invention, designated as device 100 in FIG. 10, there is a single ventricular chamber instead of two. The nondistendible jacket 102 has at least a partial trimmable margin 104 on the jacket edges. As in the other embodiment, the jacket 102 is adapted to wrap around a heart so that the ventricular chamber is adjacent to at least one ventricule of the heart. A bladder 106 has a communicable connection to the ventricular chamber 108 that is formed by a distendible membrane. A liquid supply can flow from the bladder to the ventricular chamber to increase or decrease pressure applied to the heart by the device 100. The same materials may be used to manufacture this embodiment as in the previous embodiment of device 10. Device 100 operated essentially the same as device 10, any may have chambers that cover both the right and left ventricles, or just one ventricle.

C. Examples

A model of biventricular heart failure was created by adminstering arteriovenous anastomosis ("AVA") and/or doxorubicin ("DEX") injection to dogs. The adaptive binding technique of the present invention was performed after hemodynamic examinations confirmed congestive heart failure in the dogs.

Arteriovenous anastomosis is created in a dog using the following procedure. An incision (10 cm) is made on the right side of the dog's neck just above the clavicle along the sternocleidomastoiodeus muscle. The right jugular vein and right common carotid artery is isolated, and a side-by-side anastomosis (8–10 mm) is created. Patency of the anastomoses is evaluated by auscultation (to detect continuous systolic/diastolic murmur) and palpation (to detect systolic thrill).

Cardiac binding is preferably performed eight weeks after the creation of the arteriovenous anastomosis. To perform cardiac binding, the animal is preferably placed in a supine position and a medial sternotomy is performed. The pericardium is opened and the heart and may be suspended in a cradle. A device 10 is shaped and sized to fit the heart by trimming margin 32. The heart is lifted gently and the device 10 wrapped around both the ventricles, preferably up to the pericardial reflection. As previously described, the left chamber is placed close to the left ventricle, and the right chamber close to the right ventricle. Two lateral ends of device 10 are sutured together to compress the heart just above the anterior border between the left and right ventricles. Preferably, the binding is made tight enough to follow the contour of the heart without altering hemodynamic parameters, and the free upper edge of the pouch is sutured to the pericardial flap.

The subject's heart is compressed gradually with a series of recompressions. A series of hemodynamic examinations may be performed after every heart recompression (preferably with two-dimensional echocardiography).

FIGS. 11–16 show experimental data collected from 6 dogs having a cardiac binding device 10. All data is represented as an average with a standard deviation. After the onset of heart failure (referred to as the baseline), the dogs demonstrated a considerably decreased left ventricular ejection fraction (LVEF) (from $0.61\pm0.03$ to $0.28\pm0.04$, $p<0.05$), increased left ventricular end diastolic volume (LVEDV) (from $19.7\pm4.8$ ml to $38.2\pm3.1$ ml, $p<0.05$) and left ventricular end diastolic area (LVEDA) (from $8.6\pm1.5$ cm$^2$ to $16.6\pm2.4$ cm$^2$, $p<0.05$). Also demonstrated was an increased left ventricular end systolic volume (LVESV) (from $7.6\pm0.9$ ml to $27.5\pm3.1$ ml, $p<0.05$) left ventricle end systolic area (LVESA) (from $3.5\pm0.6$ cm$^2$ to $12.6\pm1.4$ cm$^2$, $p<0.05$); and increased right atrium pressure (RAP) (from $7.1\pm0.5$ mm Hg to $14.3\pm2.2$ mm Hg, $p<0.05$).

30 minutes after cardiac binding was placed on the dog's heart, the LVEF improved to $0.35\pm0.04$, LVEDV decreased to $34.7\pm2.6$ ml, LVEDA decreased to $15.1\pm1.9$ cm$^2$; LVESV decreased to $22.5\pm2.4$ ml, LVESA decreased to $10.3\pm1.1$ cm$^2$, and RAP decreased to $13.1\pm1.9$ mm Hg (for all parameters, p was >0.05).

Sixty minutes after a total amount of 70 ml of solution was added to chambers 18, 20, the LVEF increased to $0.42\pm0.02$ ($p<0.05$ vs. binding only and vs. heart failure), LVEDV decreased to $30.1\pm3.6$ ml ($p>0.05$ vs. binding only, but $p<0.05$ vs. heart failure), LVEDA decreased to $13.1\pm1.6$ cm$^2$ (same p value), LVESV decreased to $17.4\pm2.0$ ml ($p<0.05$ vs. binding only and heart failure), LVESA decreased to $8.0\pm0.7$ cm$^2$ (same p value), and RAP decreased to $10.8\pm0.9$ mm Hg ($p>0.05$ vs. binding only, but $<0.05$ vs. heart failure). This data demonstrates that the improvement of LVEF is achieved by improving systolic function rather than diastolic function.

Sixty minutes after adding another 30 ml of liquid to chamber 18,20, all of the hemodynamic parameters improved. However, the results were statistically insignificant ($p>0.05$ vs. 60 ml liquid): $0.47\pm0.04$ (LVEF), $27.2\pm2.3$ ml (LVEDV), $12.1\pm0.9$ cm$^2$ (LVEDA), $14.4\pm1.8$ ml (LVESV), 6.6±1.0 cm² (LVESA), and 10,7±1.3 mm Hg (RAP). However, diastolic function was improved as compared to the initial binding (p<0.05).

An additional 20 ml of liquid was added to chambers 18, 20 liquid for a total of 120 ml. After sixty minutes, the additional liquid also improved all hemodynamic parameters, but was statistically insignificant (p>0.05) as compared to the previous administration of liquid.

Yet another 30 ml of liquid was added to chambers 18,20 for a total 150 ml. Sixty minutes after this liquid was added, the hemodynamics parameters of the dog's heart changed. Compression of the heart caused a decrease in the LVEDV (22.9±2.7 ml) and LVEDA (9.9±1.6 cm²). However, the systolic function and RAP showed a reverse in the previous improvement: the LVESV increased to 15.1±2.1 ml, LVESA increased to 6.9±1.3 cm², and RAP increased to 13.6±1.8 mm Hg. The impaired systolic function immediately influenced the LVEF which decreased up to 0.34±0.06 (same as after binding only). Thus, compressing the heart very rapidly (over several hours) can lead to deterioration of heart function. It is preferable that the adaptive heart remodeling be performed over a period of weeks after the heart binding is placed in the heart.

Despite the deterioration due to rapid compression, the hemodynamic parameters substantially improved when 30 ml of liquid were removed from chambers 18, 20, so that only 120 ml remained therein. Generally, the data is similar to when 120 ml was first applied to the chambers. Thus, the hemodynamic parameters may show improvement after over-compression of the heart has occurred using the heart binding.

Although the invention has been herein shown and described in what is perceived to be the most practical and preferred embodiments, it is to be understood that the invention is not intended to be limited to the specific embodiments set forth above. Accordingly, it is recognized that modifications may be made by one skilled in the art of the invention without departing from the spirit or intent of the invention and therefore, the invention is to be taken as including all reasonable equivalents to the subject matter of the appended claims.

What is claimed is:

1. A cardiac reinforcement device for constraining outward expansion of a heart during diastole, said device comprising:
    a jacket with a membrane for forming a right ventricular chamber and a separate left ventricular chamber on a single side thereof, wherein the jacket is adapted to wrap around a heart so that the right ventricular chamber is adjacent a right ventricle of the heart, and a left ventricular chamber is adjacent a left ventricle of the heart;
    a first bladder in fluid communication with the right ventricular chamber by a supply tube, wherein a first volume of liquid can flow between the first bladder and the right ventricular chamber; and
    a second bladder in fluid communication with the left ventricular chamber by a supply tube, wherein a second volume of liquid can flow between the second bladder and the left ventricular chamber;
    wherein adding or decreasing the first liquid volume or the second liquid volume will change the amount of pressure applied to the heart by the device.

2. The device of claim 1 wherein the jacket is non-distendible, and has at least a partial margin on the jacket edges.

3. The device of claim 2 wherein the membrane is distendible and conforms to the surface of the heart.

4. The device of claim 1 wherein the first bladder and the second bladder is comprised of a self-healing material to prevent leakage after being punctured by a needle.

5. A cardiac reinforcement device for constraining outward expansion of a patient's heart during diastole, said device comprising:
    a jacket with a distendible membrane for forming a right ventricular chamber and a separate left ventricular chamber on a single side thereof, the jacket having at least a partial trimmable margin on the jacket edges, wherein the jacket is adapted to wrap around a heart so that the right ventricular chamber is adjacent a right ventricule of the heart, and a left ventricular chamber is adjacent a left ventricule of the heart;
    a first bladder having a communicable connection to the right ventricular chamber;
    a second bladder having a communicable connection to the left ventricular chamber;
    wherein the first bladder and the second bladder is comprised of a self-healing material to prevent leakage after being punctured by a needle.

6. The device of claim 5 wherein a first liquid supply can flow from the first bladder to the right ventricular chamber, and a second liquid supply can flow from the second bladder to the left ventricular chamber to increase or decrease pressure applied to the heart by the device.

7. A method of adaptively binding a heart, comprising the steps of:
    placing a device behind the heart, the device comprised of a jacket having a distendible membrane thereon to form a right ventricular chamber and a left ventricular chamber;
    wrapping the jacket around the heart and fastening it closed to prevent the heart from expanding beyond a particular volume in diastole;
    periodically adjusting a fluid volume in either of the right ventricular chamber or the left ventricular chamber to prevent the heart from expanding beyond the particular volume in diastole.

8. The method of claim 7 further including the step of inserting a first bladder that is connected to the right ventricular chamber and a second bladder connected to the left ventricular chamber underneath the patient's skin so that the fluid volume can be adjusted by adding or removing fluid to the first bladder and the second bladder with a hypodermic needle.

9. The method of claim 7 further including the step of monitoring hemodynamic data corresponding the patient's heart to determine when to add or decrease fluid volume in the first or second bladder.

10. The method of claim 9 wherein the hemodynamic data is selected from the group consisting of pulmonary vein pressure, central venous pressure, right ventricular pressure, left ventricular pressure, end-diastolic volume and end-diastolic pressure.

11. The method of claim 7 wherein the fluid volume is adjusted gradually over time to avoid cardiac arrest.

12. The method of claim 7 wherein the heart has acute heart failure.

13. The method of claim 7 wherein the heart has chronic heart failure.

14. The method of claim 7 wherein the fluid volume is periodically adjusted to alter at least one measurement value of a failed heart selected from the group consisting of:

systolic aortic pressure, diastolic aortic pressure, systolic left ventricle pressure, diastolic left ventricle pressure, superior vena cava pressure, right atrium pressure, right ventricle pressure, pulmonary artery pressure, pulmonary capillary wedge pressure, diastolic volume, systolic volume, diastolic area, and systolic area.

15. A cardiac reinforcement device for constraining outward expansion of a patient's heart during diastole, said device comprising:

a jacket with a distendible membrane for forming a single ventricular chamber, the jacket having at least a partial trimmable margin on the jacket edges, wherein the jacket is adapted to wrap around a heart so that the ventricular chamber is adjacent at least one ventricule of the heart;

a bladder having a communicable connection to the ventricular chamber;

wherein the bladder is comprised of a self-healing material to prevent leakage after being punctured by a needle.

16. The device of claim 15 wherein the jacket is non-distendible.

17. The device of claim 16 wherein the membrane is distendible and conforms to at least a partial surface of the heart.

18. The device of claim 15 wherein a liquid supply can flow from the bladder to the ventricular chamber to increase or decrease pressure applied to the heart by the device.

* * * * *